May 1, 1973 M. S. SPERKA Plant Pat. 3,324
STERILE DICENTRA PLANT
Filed April 26, 1971
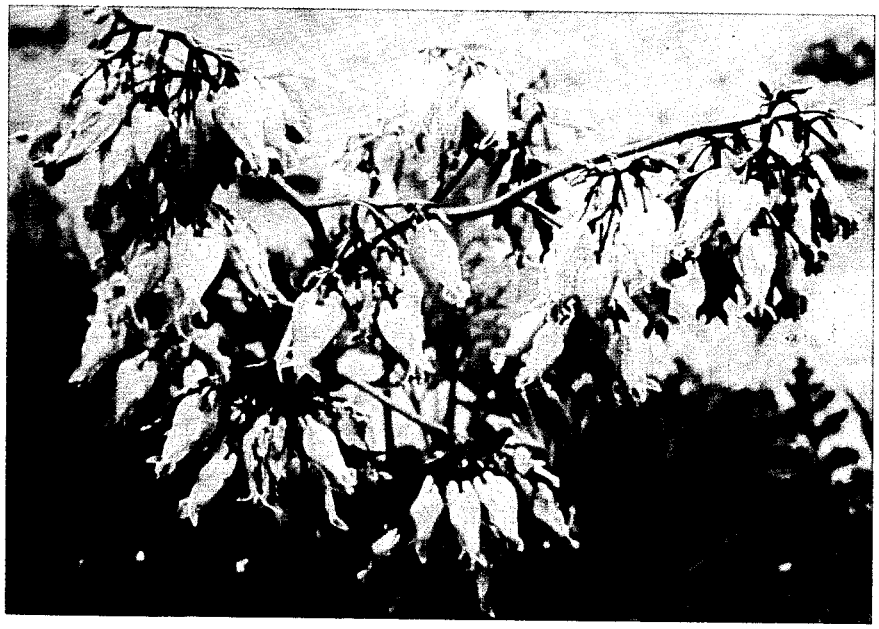
Inventor
Marie S. Sperka
By Whiteley, House & Whiteley
Attorneys United States Patent Office Plant Pat. 3,324
Patented May 1, 1973

3,324

STERILE DICENTRA PLANT

Marie S. Sperka, Rte. 2, Crivitz, Wis. 54114

Filed Apr. 26, 1971, Ser. No. 137,456
Int. Cl. A01h 5/00
U.S. Cl. Plt.—68 1 Claim

ABSTRACT OF THE DISCLOSURE

Sterile bloom of unique deep red color (more nearly true red than the bloom of any previously known bleeding heart) is produced abundantly on a vigorous and hardy plant continuously from spring until frost.

BACKGROUND OF INVENTION

The ordinary bleeding heart or Dicentra plant has bloom that is more pink than red and is not continuous, being interrupted when seed capsules are formed.

SUMMARY OF INVENTION

The novel variety of Dicentra herein disclosed is sterile. It has been asexually propagated by division of its heavy fibrous roots on which many eyes are produced each season. It does well in the central belt of the temperate zone. The foliage is vigorous and symmetrical, being larger than plants of *Dicentra "eximia"* and more vigorous than D. "Bountiful."

The bloom is profuse and literally continuous without interruption from May until killing frosts. It is a unique vibrant red in color and the extreme vigor of the plant and its continuity of bloom may be attributable to the sterility of the bloom.

DRAWING

The drawing shows the plant fragmentarily in side elevation.

I have given to this plant the name "Dicentra Luxuriant."

DETAILED DESCRIPTION

All reference to color is based on the Reinhold Color Atlas.

*Parentage*

This Dicentra is the result of open pollination. *Dicentra oregann, D. Formosa* and *D. eximia* were planted in a cultivated area in close proximity for open pollination. Only seeds produced on *D. eximia* type plants by this open pollination were sown, and the seedlings resulting from this planting were further exposed to all the Dicentra species by being planted in the immediate area. Thus they were further exposed to pollination. Most of the resulting seedlings were similar to *D. eximia,* but the few that showed different characteristics were then planted separately, and carefully observed for new and superior characteristics in foliage, blossom, and coloring of both flower and foliage. The plant herein sought to be patented was one of the seedlings thus produced. It is completely sterile and has been propagated by division.

*Root of the plant*

The plant has large vigorous, fibrous roots, capable of producing many eyes in a single season. The roots are resistant to both extreme drought and wetness, and, unprotected, have withstood temperatures as low as −35 degress F. at Crivitz, Wis. (northeastern Wisconsin). The plant is very hardy and has been covered with heavy sheets of ice without being killed.

Growth is best in well-drained sandy loam of only moderate fertility and with good drainage.

*The exposed plant structure*

This Dicentra is herbaceous, and forms a large compact bush, the foliage reaching a height of 14″ to 18″, with a spread of 24″ to 28″ for one to two year old plants. The exposed part of the plant is symmetrical, forming a bush with a regular outline. It is much larger than *D. eximia* and more robust and vigorous than D. Bountiful.

*Foliage*

The leaf stem is basal, stout and strudy and quite uniform in length, being about 9″ to 11″ exclusive of the foliage. The texture of the stem is smooth and greenish in color flushed with rose comparable to 12B7. The foliage is compoundly pinnated with serrated blunt margins. Each single main stalk has secondary stalks supporting leaflets in generally triangular over-all pattern. The texture is heavier than that of *D. eximia* and the lacy pattern of the leaflet is coarser. The top side of the emerging foliage is comparable to 29E8 and shades to 29E7 as the foliage matures. At any given time most of the foliage is mature and ranges in color from 18E6 to 293*, being dark gray-green (glaucous). The under side of each leaf is comparable in color to 29D6, shading to 29D4.

*Bud and blossoms*

The flower stalk is sturdy and, like the leaft stalk, is tinted with lineal markings which are more distinct on the flower stalk. The color of these markings is comparable to 12B4 to 12B5, becoming more intense and darkening upwardly to a color comparable to 12E6. The flower-bearing stalk usually forks four times. Each flowering stalk bears 50 to 70 bangles, or blooms. There may be as many as 50 to 60 flower stalks at a time on large one to two year old plants. The bangles (blossoms) are terminal on the upper third of the forked flower stalk and supported pendantly on pedicels 1″ to 3½″ long, the lower pedicels being the longer and the others gradually decreasing in length upwardly. The lower pedicel usually has a small leaf at its base. The remaining pedicels have a ruby (rarely green) spur at the base.

The flowering stalks are generally upright as they emerge but tend to lean slightly outward as buds mature, then lean a little more outwardly as the bangles come into full bloom. As the blossoms drop, the flower stalks lean still further outwardly, gradually disappearing in the foliage.

This Dicentra is always neat in appearance. Since it is completely sterile, there are no spent flowers and no seed pods to remove at any time.

The bloom is continuous from late spring until killing frost in the fall. The flowers hold their color well when cut.

A newly severed and planted division usually comes into full bloom by mid-season of the first growing season.

*The reproductive organs*

This plant is completely sterile, and never has set a seed pod. Because this Dicentra is completely sterile, it loses none of its vigor by producing seeds, but rather it blooms more abundantly and continuously in profusion, without letup.

*The flower*

The main body of the flower has many color phases at its various stages of development to blend into one harmonious hue that is vibrant, seemingly iridescent. The small buds are a vibrant red, comparable to 11C8, and shading as they mature to color comparable to 12A8, the base of the bud being comparable to 12B8.

As the bangles develop into full bloom the shading is comparable to 12B8 to 12B7, shading to 12B6 to 12B5 when about to drop. The over-all color of a plant, viewed at a few feet or at a distance, is glowing and vibrant, the profusion of blossoms seeming to be aglow above the glaucous green foliage.

The spurs of the mature bangles are comparable to 12E6, and the winglike section formed by the crests of the inner petals and extending forwardly and rearwardly of the bangle at the bottom is comparable to 12D6. The small triangular portion appearing in the center of the lower tip of the bangle, and surrounded by the crest is comparable to 1B4, a grayish yellow, suggestive of pale chartreuse.

The color of the heartlike cap at the juncture of the stem and the bangle is comparable to 12E8, ruby shading to 12D6 to 12C4 when the blosssom is about to drop.

The color of the flower is very distinctive as compared with any Dicentra with which I am familiar. In general appearance, it is a much deeper and brighter red than any other bleeding heart with which I am acquainted, including some that are sold as "red."

The points at which the Dicentra herein disclosed is distinctive are multiple:

(1) The blossoms are a deeper and more intense and vibrant red than any bleeding heart known to me, including those which have been advertised as "red bleeding hearts." The vibrant color of the blossoms of this plant appears only imperfectly in the print herein provided.

(2) The plant is exceptionally vigorous both in foliage and in abundance of bloom and the continuity of bloom from spring until the plant is cut down by frost in the fall.

(3) The flower is sterile and the plant can be reproduced only asexually. The sterility of the bloom is believed to be responsible for the neat over-all appearance of the plant and for its blooming strength, there being no seed capsules and no diversion of energy to production of seeds.

I claim:

1. A new variety of Dicentra as herein disclosed.

No references cited.

ROBERT E. BAGWILL, Primary Examiner